United States Patent [19]
Rizzi et al.

[11] 4,452,806
[45] Jun. 5, 1984

[54] TREATING DIABETIC COMPLICATIONS WITH 5-(SUBSTITUTED PHENYL)HYDANTOINS

[75] Inventors: James P. Rizzi, Waterford; Rodney C. Schnur, Noank, both of Conn.

[73] Assignee: Pfizer Inc., New York, N.Y.

[21] Appl. No.: 438,199

[22] Filed: Nov. 1, 1982

[51] Int. Cl.³ .................. A61K 31/415; C07D 233/76; C07D 233/78
[52] U.S. Cl. ............................... 424/273 R; 548/309; 548/314; 562/432; 568/41; 568/55
[58] Field of Search .............................. 548/314, 309; 424/273 R

[56] References Cited

FOREIGN PATENT DOCUMENTS 40-9151  5/1965  Japan .................................. 548/314
2053206  2/1981  United Kingdom ................ 548/314

Primary Examiner—Richard A. Schwartz
Attorney, Agent, or Firm—Charles J. Knuth; Albert E. Frost; Mark Dryer

[57] ABSTRACT

A series of 5-(substituted phenyl)hydantoins and pharmaceutically acceptable salts thereof are aldose reductase inhibitors useful as agents for treatment of chronic diabetic complications; intermediates therefore; and processes for preparation of said compounds.

20 Claims, No Drawings

TREATING DIABETIC COMPLICATIONS WITH 5-(SUBSTITUTED PHENYL)HYDANTOINS

BACKGROUND OF THE INVENTION

This invention relates to novel 5-(substituted phenyl)-hydantoins and to pharmaceutically acceptable salts thereof as inhibitors of aldose reductase useful as therapeutic agents for the treatment of chronic diabetic complications; and to intermediates therefor.

Despite the widespread use of insulin and of the availability of a large number of synthetic hypo-glycemic agents such as the sulfonylureas (e.g. chlorpropamide, tolbutamide, acetohexamide) and biguanides (e.g. phenformin), the search for improved hypoglycemic agents continues. More recently, efforts have been directed to controlling certain chronic complications of diabetes, such as diabetic cataracts, neuropathy and retinopathy. Such efforts have given rise to development of aldose reductase inhibitors, compounds which inhibit the activity of the enzyme aldose reductase which is primarily responsible for regulating reduction of aldoses to the corresponding polyols. In this way, unwanted accumulation of galactitol in the lens of galactosemic subjects and of sorbitol in the lens, kidney and peripheral nervous cord of various diabetic subjects is prevented or reduced. References which describe aldose reductase inhibitors are U.S. Pat. No. 3,821,383—1,3-dioxo-1H-benz[d,e]-isoquinoline-2(3H)-acetic acid and related compounds; U.S. Pat. No. 4,200,642—spiro-oxazolidine-2,4-diones; U.S. Pat. Nos. 4,117,230; 4,130,714; 4,147,797; 4,210,756; 4,235,911 and 4,282,229, each of which describes certain spirohydantoins; and the concurrently filed application of Schnur, entitled "Aldose Reductase Inhibiting 5-(2-Alkoxy-3-Substituted Phenyl)Hydantoins", and identified by the U.S. Ser. No. 438,200.

U.S. Pat. No. 4,281,009 describes a series of 5,5-disubstituted hydantoins in which one substituent is a substituted phenyl group and the other an alkyl or a heterocyclic group, said compounds being useful for treatment of diseases caused by stress.

Henze et al., J. Am. Chem. Soc. 64, 522-3 (1942) describe 5-phenylhydantoin and certain 5-(mono- and di-substituted phenyl)hydantoins wherein the substituents are hydroxy, alkoxy, formyl, methyl, chloro or dimethylamino. Other 5-(substituted phenyl)hydantoins are disclosed in U.S. Pat. No. 3,410,865 and in British Patent Application No. 2,063,206A. None of these known 5-(phenyl)hydantoins are reported to be aldose reductase inhibitors or to have a thio, sulfinyl or sulfonyl substituent in the phenyl ring.

SUMMARY OF THE INVENTION

It has now been found that certain 5-(substituted) phenyl hydantoins of formula I below and pharmaceutically acceptable salts thereof are aldose reductase inhibitors useful as therapeutic agents for preventing and/or alleviating chronic diabetic complications.

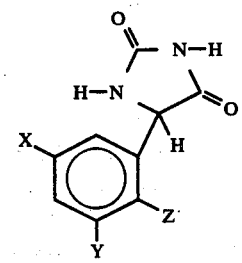

In formula (I), each of X and Y is hydrogen, chloro, fluoro, bromo, $(C_{1-6})$alkyl, $(C_{1-6})$alkoxy, trifluoromethyl, amino or nitro;

Z is $S(O)_mR$ or $SO_2NHR^1$;

m is 0, 1 or 2;

R is hydrogen, $(C_{1-6})$alkyl, chloro, methoxymethyl or

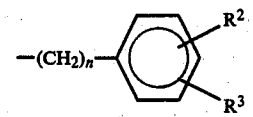

n is an integer of from 1 to 4;

each of $R^2$ and $R^3$ is hydrogen, chloro, fluoro, bromo, $(C_{1-6})$alkyl, $(C_{1-6})$alkoxy, amino or nitro;

$R^1$ is hydrogen, furfuryl,

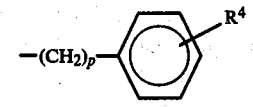

$(C_{1-6})$alkyl, omega-substituted $(C_{2-6})$alkyl wherein the substituent is hydroxy or dimethylamino; $R^4$ is hydrogen, fluoro or chloro; and p is 0 or an integer of from 1 to 4; provided that when R is chloro, m is 2.

The favored compounds of formula I are those wherein Z is $S(O)_mR$; m is 2; and R is $(C_{1-6})$alkyl or

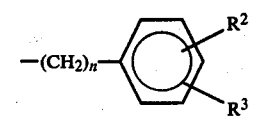

n is 1 or 2; and those wherein Z is $SO_2NHR^1$ wherein $R^1$ is furfuryl or

wherein $R^4$ is fluoro or chloro. The preferred compounds are those favored compounds wherein X is fluoro or chloro; Y is hydrogen, fluoro, chloro or methyl, and Z is $-SO_2CH_3$,

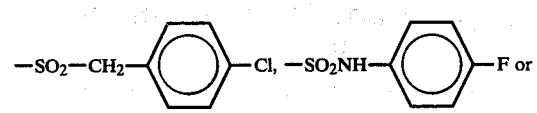

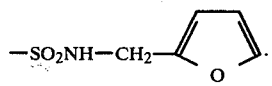

The present invention also includes the pharmaceutically acceptable acid addition salts of those compounds of formula I wherein X and or Y is amino. Representative of said salts, but not limited thereto are the hydrochloride, hydrobromide, sulfate, phosphate, nitrate, acetate, lactate, citrate, malate, succinate and gluconate. Such salts are prepared by contacting the free base with the appropriate mineral or organic acid in either aqueous solution or in a suitable organic solvent. The solid salt is then obtained by precipitation or by evaporation of the solvent.

Because of the acidic hydrogen atom in the hydantoin ring of the compounds of formula I, salts can be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and the solution subsequently evaporated to dryness. Suitable pharmaceutically acceptable cations for this purpose include, but are not limited to, potassium, sodium, ammonium, calcium and magnesium, aluminum, benzathine, piperazine, N-methylglucamine and procaine.

It is to be understood that by use of the term pharmaceutically acceptable salts in the disclosure and claims hereof it is meant to embrace both the acid addition salts and the salts formed with appropriate cations, as described above.

Also embraced by the present invention are pharmaceutical compositions comprising a pharmaceutically acceptable carrier and a compound of formula I in an amount effective for the treatment of diabetes-associated complications, including diabetic cataracts, neuropathy and retinopathy. Preferred compounds for use in such pharmaceutical compositions are those having the preferred substituents as defined herein above.

The present invention further includes a method of treatment of diabetes-associated complications, including diabetic cataracts, neuropathy and retinopathy, comprising administering to a subject in need of treatment an effective amount of a compound of formula I, preferably a compound having the preferred substituents for X, as defined herein above.

DETAILED DESCRIPTION OF THE INVENTION

The compounds of this invention wherein Z is $S(O)_mR$ are prepared by reaction sequence A:

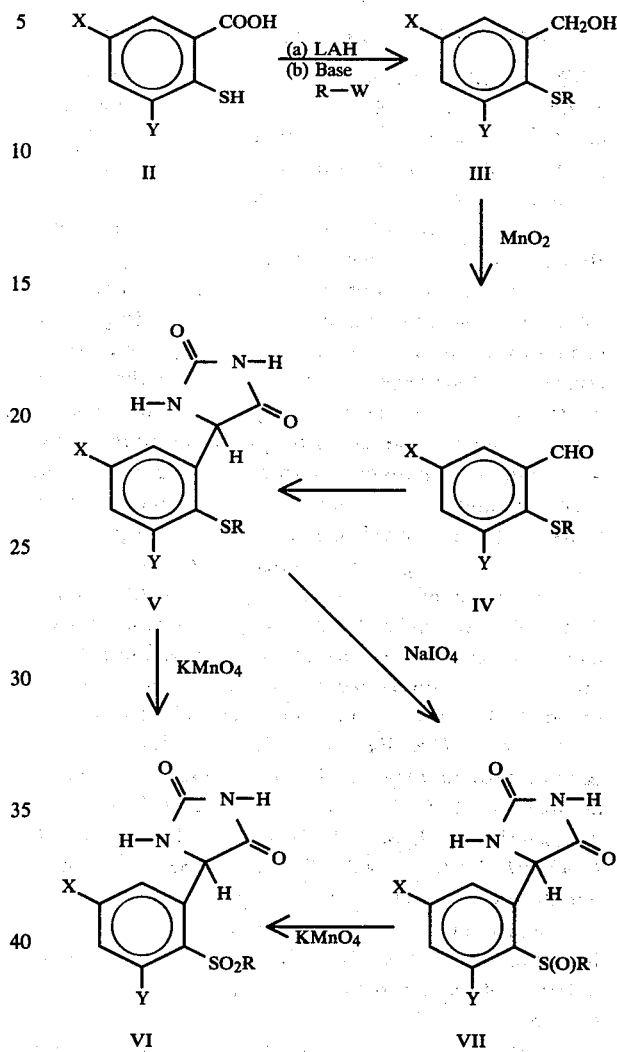

Formula I compounds wherein Z is $SO_2NHR^1$ are prepared according to sequence B:

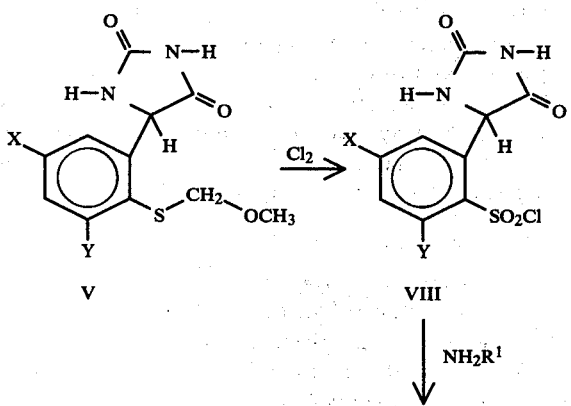

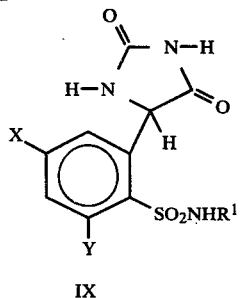

Convenient starting materials for sequence A are the appropriate 2-mercaptobenzoic acid derivatives of formula II or the 2-mercaptobenzaldehydes of formula IV. Many of the required benozic acid or benzaldehyde derivatives are known compounds. Those that are not described in the literature are readily preparable by methods known to those skilled in the art.

In the first step of sequence A, the appropriate 2-mercaptobenzoic acid (formula II) is reduced to the corresponding 2-mercaptobenzyl alcohol derivatives by direct reduction of the carboxyl group using lithium aluminum hydride (LAH). The reduction is conducted in a reaction-inert solvent such as a dialkyl ether, a cyclic ether, e.g. diethyl ether, dioxane, tetrahydrofuran, ethyleneglycol dimethyl ether and diethyleneglycol dimethyl ether, and at a temperature of from about $-10°$ C. to $+30°$ C. In general, the compound to be reduced is added to a solution or slurry of the reagent. An excess of reagent, up to 25% excess, is usually used to insure complete reduction. The unreacted and/or excess reagent is destroyed by addition of ethyl acetate. The reduction product is isolated by known procedures.

In addition to lithium aluminum hydride, other hydride reducing agents such as diisobutyl aluminum hydride, sodium diethyl aluminum hydride and sodium bis(2-methoxyethoxy)aluminum hydride can be used to reduce the benzoic acid starting material to the corresponding benzyl alcohol.

In the case of each of the above mentioned reducing agents, acid chloride, ester and anhydride derivatives of the 2-mercaptobenzoic acid reagent (II) can be used in place of said 2-mercaptobenzoic acid as starting material.

The next step, alkylation or aralkylation of the mercapto group is achieved by reacting the 2-mercaptobenzyl alcohol (III) in a reaction-inert solvent with the appropriate alkylating or aralkylating agent R-W in the presence of a base. The group R is as defined above and W is chloro, bromo or iodo, or tosylate.

Suitable bases for the alkylation or aralkylation are alkoxides, hydrides and hydroxides of sodium and potassium; organic bases such as trialkylamines, pyridine, dimethylaniline and N-methylmorpholine.

The alkylating or aralkylating agent and the mercaptobenzyl alcohol (III) are reacted in molar ratios ranging from equimolar to up to 10% excess of said agent. Greater excesses of said agent offer no advantage and are generally avoided for reasons of economy. The amount of base used is at least equal to the amount of mercaptobenzyl alcohol reactant. The thus-produced thioether derivative is then oxidized to the corresponding benzaldehyde (IV) by means of activated manganese dioxide in a reaction-inert solvent at temperatures ranging from about 20° C. to about 100° C. In most instances ambient temperature is used. Suitable reaction-inert solvents are methylene chloride, chloroform, acetone, dioxane, tetrahydrofuran, benzene and toluene. An excess of manganese dioxide, generally from 4 to 15 equivalents, is used in order to ensure complete reaction. The reaction period, of course, depends upon the reaction temperature, the amount of oxidizing agent used, and upon the nature of the compound to be oxidized. In general, reaction periods of from about 4 hours to 24 hours are required. The oxidized product (IV) is recovered by known methods as by filtration to remove the excess $MnO_2$, and evaporation of the filtrate under reduced pressure to afford the crude benzaldehyde derivatives (IV). Said benzaldehyde derivatives are generally used without further purification in sequence A.

The benzaldehyde derivative (IV) is converted to the hydantoin (V) by reaction with ammonium carbonate and potassium (or sodium) cyanide in aqueous alcohol solution at a temperature of from 50°–60° C. for from 2 to 24 hours. Molar ratios of benzaldehyde reactant:potasium (or sodium) cyanide:ammonium carbonate of from 1:2:4 afford satisfactory yields of the desired hydantoin. The product is recovered by acidifying the reaction mixture and extracting it with a water-immiscible solvent such as ethyl acetate.

The hydantoin thioether compound (V) is then oxidized to the corresponding sulfone (VI) directly or stepwise via the intermediate sulfoxide (VII). The stepwise oxidation is carried out by treating the thioether (V) with sodium periodate in aqueous alcoholic solution at ambient temperature using a 1:2 molar ratio of thioether to sodium periodate. The product, a mixture of diastereomeric sulfoxides (VIII) is recovered by extraction with a water-immiscible solvent, e.g. ethyl acetate.

Direct oxidation of the thioether (V) to the corresponding sulfonyl derivative (VI) is conveniently carried out by reacting the thioether with potassium permanganate in acetic acid at a temperature of from about $-10°$ to room temperature. Two moles of permanganate are used per mole of thioether. The product is recovered by quenching the reaction mixture in dilute aqueous sodium bisulfite and extraction of the product therefrom with a water-immiscible solvent such as ethyl acetate.

Alternatively, the sulfonyl derivative (VI) is prepared by potassium permanganate oxidation of the sulfoxide (VII). The procedure used is, except for the use of an equimolar amount of permanganate, the same as that described for the direct thioether to sulfonyl derivative conversion.

In sequence B, compounds of formula (VIII), which serve as intermediates for the sulfonamido derivatives of formula (IX), are prepared from a compound of formula (V) wherein R is methoxymethyl by reacting said compound with chlorine in a reaction-inert solvent. In a typical example, chlorine gas is passed into a solution of the methoxymethylthio ether (V) in a water-miscible solvent-water medium at 0° C. to 20° C. until a yellow color persists. The reaction mixture is quenched by adding it to dilute aqueous sodium bisulfite and the product recovered therefrom by extraction. Suitable solvents for this reaction are dioxane, tetrahydrofuran, 1,2-dimethoxyethane (monoglyme) and diethyleneglycol dimethyl ether (diglyme).

The sulfonyl chlorides of formula (VIII) are converted to sulfonamides of formula (IX) by reacting them with the appropriate amine of formula $H_2NR^1$ in a reaction-inert solvent at from 0° C. to 50° C. until reaction is complete. A variety of solvents can be used such as methylene chloride, chloroform, dioxane, tetrahydrofuran, monoglyme, diglyme and alcohols. The products are recovered by quenching the reaction mixture in dilute aqueous acid followed by extraction of the resulting solution with a water-immiscible solvent, such as ethyl acetate.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention or alleviation of such conditions. The compounds may be administered to a subject in need of treatment by a variety of conventional routes of administration, including oral, parenteral and topical. In general, these compounds will be administered orally or parenterally at dosages between about 0.25 and 25 mg/kg body weight of the subject to be treated per day, preferably from about 1.0 to 10 mg/kg. However, depending on the condition of the subject being treated, some variation in dosage will necessarily occur. The person responsible for administration will, in any event, determine the appropriate dose for the individual subject.

The novel compounds of this invention can be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate can be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, together with diluents such as water, ethanol, propylene glycol, glycerine and combinations thereof.

For parenteral administration, solutions of the novel compound of formula I in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The higher solubility of the present compounds of formula I and of the pharmaceutically acceptable salts thereof in aqueous solution, compared to other similar compounds and especially compared to the corresponding compounds of formula I having no amino or substituted amino substituents, is advantageous not only for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, PA). The ophthalmic preparation will contain a compound of formula I or a pharmaceutically acceptable salt thereof in a concentration from about 0.1 to about 5% by weight, preferably from about 0.5 to about 2% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potassium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinvylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized (i.e. diabetic) rats; (3) measuring their ability to reverse already elevated sorbitol levels in the sciatic nerve and lens of chronic streptozotocin-induced diabetic rats; (4) measuring their ability to prevent or inhibit galactitol formation in the lense of acutely galactosemic rats; and (5) measuring their ability to delay cataract formation and reduce the severity of lens opacities in chronic galactosemic rats. Suitable experimental procedures are described in U.S. Pat. No. 3,821,383 and the references cited therein.

In the examples which follow, no effort was made to optimize the yields of a given reaction. All nuclear magnetic resonance data (NMR) are in standard notation and are reported in parts per million (ppm) downfield from trimethylsilane. Deuterated dimethylsulfoxide (DMSO-$d_6$) was used as solvent in all examples.

EXAMPLE 1

4-Chloro-2-Hydroxymethylthiophenol

A solution of 4-chloro-2-mercaptobenzoic acid (40.0 g, 0.21 mol) in dry tetrahydrofuran (250 ml) was added dropwise to a slurry of lithium aluminum hydride (10.0 g, 0.26 mol) in dry tetrahydrofuran (50 ml) at 0° C. Following completion of addition, the reaction mixture was allowed to warm to room temperature, then stirred for 3 hours at said temperature. It was cooled to 0° C. and ethyl acetate (40 ml) added to quench excess lithium aluminum hydride. The quenched reaction was stirred for 30 minutes then cautiously treated with water (10 ml), followed by 1 N sodium hydroxide (40 ml). The aluminum salts which precipitated were filtered off, dissolved in 10% hydrochloric acid and the solution extracted with ethyl acetate. The extract was combined with the filtrate (from the aluminum filtration) and washed successively with 10% hydrogen chloride, water and brine. It was dried (MgSO$_4$) and evaporated under reduced pressure to give the title product as an oily solid; 35.0 g, 94% yield.

It was used as is in the following Example.

EXAMPLE 2

5-Chloro-2-Thiomethylbenzaldehyde

Sodium methoxide (11.5 g, 0.21 mol) was added to a solution of 4-chloro-2-hydroxymethylthiophenol (35.0 g, 0.20 mol) in N,N-dimethylformamide (300 ml) at 0° C. The mixture was stirred for 30 minutes at 0° C. and then iodomethane (15 ml, 0.24 mol) added. The mixture was stirred an additional 30 minutes and then poured into water (500 ml) and the product extracted therefrom with ether. The extract was washed successively with water and brine then dried (MgSO$_4$). Evaporation of the dried extract under reduced pressure gave a yellow solid.

The yellow solid was dissolved in methylene chloride (600 ml), manganese dioxide (250 g) added and the mixture stirred at room temperature for 6 hours. Filtration of the reaction mixture and evaporation of the filtrate under reduced pressure gave 33.0 g (89% yield) of the title product as an oily solid. It was used as is in the following Example.

EXAMPLE 3

5-(5-Chloro-2-thiomethylphenyl)hydantoin

A mixture of 5-chloro-2-thiomethylbenzaldehyde (33.0 g, 0.18 mol), potassium cyanide (23.0 g, 0.36 mol), ammonium carbonate (68.0 g, 0.71 mol) and 20% aqueous ethanol (1200 ml) was heated at 60° C. for 24 hours. It was then cooled and carefully poured into 10% hydrogen chloride (1000 ml) and the product extracted from the resulting mixture with ethyl acetate. The extract was washed with water, then with brine and dried (MgSO$_4$). Removal of the solvent under reduced pressure gave a partially solidified oil. Trituration of this residue with ether afforded 27.5 g (60% yield) of an off-white solid. M.P.=183°–185° C.

Analysis:

Calc'd. for $C_{10}H_9N_2O_2SCl$: 46.79% C; 3.53% H; 10.91% N Found: 46.91% C; 3.65% H; 10.58% N.

MS: 256 (M+), 209 (100%), 170.

The following compounds were prepared in like manner from the appropriate thiobenzaldehyde derivative of formula (IV) above:

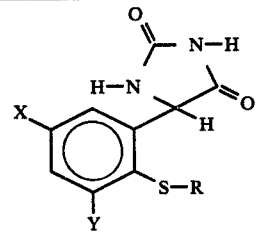

| X | Y | R | Isolation-Triturate | Calc'd. Found C | H | N | Mass Spec. (MS) | M.P. (°C.) | 250 MHz NMR |
|---|---|---|---|---|---|---|---|---|---|
| H | H | CH$_3$ | 1:1 ether-hexane | 54.56<br>54.04 | 4.53<br>4.56 | 12.60<br>12.53 | 222(M+,100%)<br>175,164,136 | 137–139 | |
| H | H | CH$_2$CH$_3$ | 1:1 ether-hexane | 55.92<br>55.86 | 5.12<br>5.06 | 11.86<br>11.75 | | 136–137 | 10.5(bs,1H),8.31(s,1H),<br>7.55(d,2H,J=8Hz),7.4–<br>7.20(M,3H),5.58(s,1H),<br>2.95(q,2H,J=8Hz),1.21<br>(t,3H,J=8Hz) |
| H | H | (CH$_2$)$_2$CH$_3$ | * | 57.58<br>57.69 | 5.64<br>5.68 | 11.19<br>11.19 | | 127–129 | 10.81(bs,1H),8.30(s,<br>1H),7.53(d,1H,J=Hz),<br>7.39–7.24(m,3H),5.58<br>(s,1H),3.01–2.82(m,2H), |

-continued

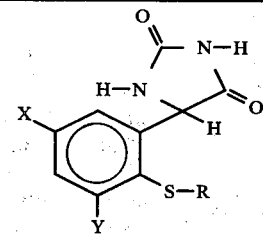

| X | Y | R | Isolation-Triturate | Calc'd. Found C | H | N | Mass Spec. (MS) | M.P. (°C.) | 250 MHz NMR |
|---|---|---|---|---|---|---|---|---|---|
| H | H | $(CH_2)_3CH_3$ | 1:1 ether-hexane | 59.07 / 59.30 | 6.10 / 5.92 | 10.59 / 10.53 | 264(M+,100%), 208,207,195, 136 | 100–103 | 1.65–1.44(m,2H),0.95 (s,3H,J=Hz) |
| Cl | H | $CH_2OCH_3$ | 1:1 $CH_2Cl_2$–hexane | 46.08 / 46.13 | 3.87 / 3.99 | 9.77 / 9.84 | 286(M+),254 (100%),211, 209,183,170 | 159–161 | |
| Cl | H | $CH_2$—4-$ClC_6H_4$ | 4:1 ether-hexane | 52.32 / 52.55 | 3.29 / 3.31 | 7.62 / 7.49 | 366(M+),241, 170,125(100%) | 139–140 | |
| Cl | H | $(CH_2)_2$—4-$ClC_6H_4$ | 1:1 $CH_2Cl_2$–hexane | 53.55 / 53.64 | 3.70 / 3.86 | 7.34 / 7.57 | | 184–186 | 10.92 (bs, 1H), 8.37(s,1H),7.62(d,1H, J=8Hz),7.45(d,J=8Hz), 7.40–7.30(m,3H),7.25 (d,2H,J=8Hz),5.55(s, 1H),3.32–3.13(m,2H), 2.90–2.70(m,2H) |
| Cl | $CF_3$ | $CH_3$ | i-propyl-ether | 40.67 | 2.67 | 8.41 | | 244–245 | 11.05(bs,1H),8.40(s, 1H),7.94(s,1H),7.75 (s,1H),6.09(s,1H),2.40 (s,3H) |

*Chromatography on silica gel, elution with 60:40 hexane-ethyl acetate.

EXAMPLE 4

5-(5-Chloro-2-Methylsulfinylphenyl)hydantoin

To a solution of 5-(5-chloro-2-thiomethylphenyl)-hydantoin (1.0 g, 3.9 mmol) in ethanol (50 ml) was added water (8 ml) and sodium periodate (1.7 g, 7.8 mmol) at room temperature. The mixture was stirred overnight then poured into water (50 ml) and the product extracted therefrom with ethyl acetate. The extract was dried over $MgSO_4$ and evaporated at reduced pressure to give 0.4 g (37% yield) of a white solid comprising a mixture of diastereomeric sulfoxides. M.P. 165°–170° C.

Similarly, the following compounds were prepared from the corresponding 5-(2-(RS)-phenyl)hydantoins of formula (V) above:

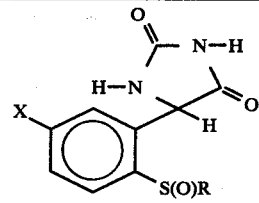

| X | R | Isolation-Trituration | Calc'd. Found % C | % H | % N | IR (cm$^{-1}$) S>O Stretch | MP (°C.) |
|---|---|---|---|---|---|---|---|
| H | $CH_2CH_3$ | i-propyl ether | | | | 1012 (bs) | 119–120 |
| H | $(CH_2)_2CH_3$ | i-propyl ether | | | | 1009 (br) | 116–118 |
| H | $(CH_2)_3CH_3$ | i-propyl ether | | | | 1014 (br) | 125–130 |
| H | $CH(CH_3)_2$ | i-propyl ether | | | | 1013 (br) | 127–130 |
| Cl | $CH_2$—4-$ClC_6H_4$ | 1:1 water-acetic acid | | | | 1016 (br) | 165–170 |
| Cl | $(CH_2)_2$—4-$ClC_6H_4$ | i-propyl ether | 51.40 / 51.25 | 3.55 / 3.77 | 7.05 / 7.25 | 1015 (br) | 140–144 |

EXAMPLE 5

5-(5-Chloro-2-Methylsulfonylphenyl)hydantoin

Potassium permanganate (11.0 g, 0.07 mol) and water (10 ml) were added to a slurry of 5-(5-chloro-2-thiomethylphenyl)hydantoin (9.0 g, 0.035 mol) in glacial acetic acid (100 ml) at 0° C. The reaction mixture was stirred at 0° C. for a half hour then poured into 500 ml of a 10% solution of sodium bisulfite in water. The product was extracted therefrom with ethyl acetate, the extract washed with water and brine, then dried (MgSO$_4$) and evaporated under reduced pressure. The white solid residue was triturated with ether, filtered and air dried. Yield=8.5 g (84%) of title product; m.p. 238°–240° C.

Analysis:

Calcd. for C$_{10}$H$_9$N$_2$O$_4$SCl: 41.60% C; 3.14% H; 9.70% N. Found: 41.37% C; 3.39% H; 9.43% N.

MS: 288, 289, 209 (100%), 202.

The following compounds are made in like manner from appropriate 5-(2-(RS)-phenyl)hydantoins of formula (V):

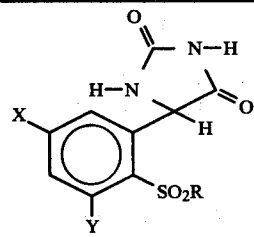

| X | Y | R | Isolation-Trituration | Calc'd. Found %C | %H | %N | MP (°C.) | 250 MHz NMR |
|---|---|---|---|---|---|---|---|---|
| Cl | H | CH$_2$CH$_3$ | i-propyl ether | 43.64 43.75 | 3.66 3.78 | 9.25 8.93 | 218–219 | 11.11 (bs, 1H), 8.53 (s, 1H), 8.00 (d, 1H, J = 8 Hz), 7.77 (d, 1H, J = 8 Hz), 7.59 (s, 1H), 6.23 (s, 1H), 3.63–3.46 (m, 2H), 1.18 (t, 3H, J = 8 Hz) |
| Cl | H | (CH$_2$)$_2$CH$_3$ | i-propyl ether | 45.50 45.23 | 4.14 4.19 | 8.84 8.65 | 188–189 | 11.10 (bs, 1H), 8.55 (s, 1H), 8.00 (d, 1H, J = 8 Hz), 7.77 (d, 1H, J = 8 Hz), 7.59 (s, 1H), 6.22 (s, 1H), 3.62–3.44 (m, 2H), 1.78–1.42 (m, 2H), 0.95 (t, 3H, J = 8 Hz) |
| Cl | H | CH(CH$_3$)$_2$ | i-propyl ether | 45.50 45.58 | 4.14 4.21 | 8.84 8.49 | 221–222 | 11.10 (bs, 1H), 8.57 (s, 1H), 7.98 (d, 1H, J = 8 Hz), 7.78 (d, 1H, J = 8 Hz), 7.60 (s, 1H), 6.19 (s, 1H), 3.83–3.67 (m, 1H), 1.32 (d, 3H, J = 8 Hz), 1.10 (d, 3H, J = 8 Hz) |
| F | H | CH$_3$ | i-propyl ether | 44.12 44.12 | 3.33 3.49 | 10.29 9.89 | 222–224 | 11.10 (bs, 1H), 8.53 (s, 1H), 8.18–8.00 (m, 1H), 7.85–7.40 (m, 2H), 6.34 (s, 1H), 3.45 (s, 3H) |
| F | | CH$_2$CH$_3$ | ether | | | | 183–186 | 11.08 (bs, 1H), 8.55 (s, 1H), 8.10–8.04 (m, 1H), 7.60–7.38 (m, 2H), 6.25 (s, 1H), 3.60–3.48 (m, 2H), 1.16 (t, 3H, J = 8 Hz) |
| F | | (CH$_2$)$_2$CH$_3$ | * | 47.99 47.94 | 4.33 4.34 | 9.32 9.28 | 164–166 | 11.05 (bs, 1H), 8.50 (s, 1H), 8.06–8.00 (m, 1H), 7.52–7.35 (m, 2H), 6.20 (s, 1H), 3.56–3.40 (m, 2H), 1.75–1.39 (m, 2H), 0.90 (t, 3H, J = 8 Hz) |
| Cl | H | CH$_2$—4-ClC$_6$H$_4$ | 1:1 water-acetic acid | | | | 165–167 | |
| Cl | H | (CH$_2$)$_2$—4-ClC$_6$H$_4$ | water | | | | 229–231 | 11.11 (bs, 1H), 8.56 (s, 1H), 8.00 (d, 1H, J = 8 Hz), 7.74 (d, 1H, J = 8 Hz), 7.60 (s, 1H), 7.31 (s, 4H), 6.27 (s, 1H), 4.00–3.70 (m, 2H), 3.10–2.75 (m, 2H) |
| Cl | Cl | CH$_3$ | ether | | | | 225–227 | 11.05 (bs, 1H), 8.35 (s, 1H), 8.13 (s, 1H), 7.62 (s, 1H), 6.81 (s, 1H), 3.58 (s, 3H) |
| Cl | CH$_3$ | CH$_3$ | ether | 43.64 43.72 | 3.66 3.77 | 9.25 9.14 | 258–259 | 11.02 (bs, 1H), 8.40 (s, 1H), 7.66 (s, 1H), 7.40 (s, 1H), 6.72 (s, 1H), 3.45 (s, 3H), 2.70 (s, 3H) |
| Cl | CF$_3$ | CH$_3$ | i-propyl ether | | | | 231–233 | 11.13 (bs, 1H), 8.52 (s, 1H), 8.20 (s, 1H), 7.95 (s, 1H), 6.61 (s, 1H), 3.57 (s, 3H) |

*Chromatography on silica gel, elution with 60–40 hexane-ethyl acetate.

EXAMPLE 6

5-(5-Chloro-2-chlorosulfonylphenyl)hydantoin

A solution of 5-(5-chloro-2-thiomethoxymethylphenyl)hydantoin (3.5 g, 0.012 mol) in dioxane (175 ml) and water (50 ml) was cooled to 0° C. Chlorine gas was passed through the solution at 0° C. until a yellow color persisted. The mixture was stirred for 15 minutes then poured into 200 ml of ice cold 10% aqueous sodium bisulfite solution. The product was extracted from the resulting solution with ethyl acetate, the extract washed with water, then with brine, and dried ($MgSO_4$). Evaporation under reduced pressure gave a white solid. Trituration of the solid in ether:hexane (1:1) followed by filtration gave 2.8 g (74%) yield; M.P. 211°–212° C.

250 MHz NMR: 10.92 (bs), 8.00 (bs, 1H), 7.80 (d, 1H, J=8 Hz), 7.43 (d, 1H, J=8 Hz), 7.12 (s, 1H), 6.20 (s, 1H).

EXAMPLE 7

5-(5-Chloro-2-sulfonamidophenyl)hydantoin

Ammonia gas was passed into a slurry of 5-(5-chlorosulfonylphenyl)hydantoin (5.0 g, 0.016 mol) in methylene chloride (100 m) at 0° C. until the mixture became homogeneous and yellow in color. Stirring at 0° C. was continued for one hour after which the reaction mixture was poured into 10% hydrogen chloride (200 ml) and the product extracted therefrom with ethyl acetate. The extract was washed successively with water, 10% hydrogen chloride, water and brine and then dried ($MgSO_4$). Evaporation of the dried extract under reduced pressure followed by trituration of the residue with ethyl acetate gave 2.7 g (59%) of a white solid. M.P. 239°–240° C.

Analysis:

Calcd. for $C_9H_8N_3O_4SCl$: 37.31% C; 2.78% H; 14.49% N Found: 37.62% C; 2.99% H; 14.11% N.

250 MHz NMR: 11.08 (bs, 1H), 8.44 (s, 1H), 7.97 (d, 1H, J=8 Hz), 7.69 (d, 1H, J=8 Hz), 7.63 (bs, 2H), 7.46 (s, 1H), 6.13 (s, 1H).

The following compounds are similarly prepared from the appropirate amine and 5-(2-chlorosulfonylphenyl)hydantoin of formula (VIII) above:

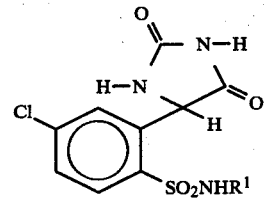

| $R^1$ | Isolation-Trituration | Calc'd. Found | | | MP (°C.) | 250 MHz NMR |
|---|---|---|---|---|---|---|
| | | % C | % H | % N | | |
| $CH_3$ | 1:1 ether-hexane | 39.55<br>39.61 | 3.32<br>3.38 | 13.83<br>13.61 | 205–207 | 11.09 (bs, 1H); 8.50 (s, 1H); 7.95 (d, 1H, J = 8 Hz); 7.69 (d, 1H, J = 8 Hz); 7.61 (bs, 1H); 7.50 (s, 1H); 6.08 (s, 1H); 2.49 (s, 3H) |
| $(CH_2)_2CH_3$ | ether | | | | 162–163 | 11.01 (bs, 1H); 8.42 (s, 1H); 7.90 (d, 1H, J = 8 Hz); 7.67–7.58 (m, 2H); 7.45 (s, 1H); 6.06 (s, 1H); 2.73 (t, 2H, J = 6 Hz); 1.48–1.31 (m, 2H); 0.78 (t, 3H, J = 6 Hz) |
| $(CH_2)_3CH_3$ | ether | 45.16<br>45.37 | 4.66<br>4.74 | 12.14<br>11.82 | 169–171 | 11.06 (bs, 1H); 8.50 (s, 1H); 7.93 (d, 1H, J = 8 Hz); 7.70–7.60 (m, 2H); 7.50 (s, 1H); 6.12 (s, 1H); 2.82 (q, 2H, J = 6 Hz); 1.48–1.20 (m, 4H); 0.84 (t, 3H, J = 6 Hz) |
| $(CH_2)_4CH_3$ | ether | | | | 146–148 | 11.04 (bs, 1H); 8.46 (s, 1H); 7.93 (d, 1H, J = 8 Hz); 7.70–7.58 (m, 2H); 7.46 (s, 1H); 6.10 (s, 1H); 2.80 (q, 2H, J = 5 Hz); 1.50–1.16 (m, 6H); 0.81 (t, 3H, J = 5 Hz) |
| $CH_2CH_2OH$ | i-propyl ether | | | | 156–158 | 11.06 (bs, 1H); 8.45 (s, 1H); 7.95 (d, 1H, J = 8 Hz); 7.82 (t, 1H, J = 6 Hz); 7.67 (d, 1H, J = 8 Hz); 7.49 (s, 1H); 6.10 (s, 1H); 3.40 (t, 2H, J = 7 Hz); 2.88 (q, 2H, J = 7 Hz) |
| $(CH_2)_3OH$ | $CHCl_3$ | | | | 145 (foam) | 11.05 (s, 1H); 8.49 (s, 1H); 7.92 (d, 1H, J = 8 Hz); 7.71–6.63 (m, 2H); 7.49 (s, 1H); 6.09 (s, 1H); 4.46 (t, 1H, J = 5 Hz); 3.42–3.35 (m, 2H); 2.95–2.80 (m, 2H): 1.58 (quintet, q, 2H, J = 6 Hz) |
| $(CH_2)_4OH$ | i-propyl ether | 43.16<br>42.94 | 4.46<br>4.47 | 11.61<br>11.23 | | 11.05 (s, 1H); 8.48 (s, 1H); 7.93 (d, 1H, J = 8 Hz); |

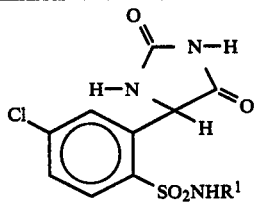

| R[1] | Isolation-Trituration | Calc'd. Found % C | % H | % N | MP (°C.) | 250 MHz NMR |
|---|---|---|---|---|---|---|
| CH$_2$CH$_2$N(CH$_3$)$_2$ | i-propyl ether | | | | 190° (foam) | 7.71–7.62 (m, 2H); 7.48 (s, 1H); 6.10 (s, 1H); 4.40 (t, 1H, J = 4 Hz); 3.40–3.20 (m, 2H); 2.81 (q, 2H, J = 5 Hz); 1.50–1.30 (m, 4H) 11.00 (bs, 1H); 9.00–8.20 (b.M, 2H); 7.95 (d, 1H, J = 8 Hz); 7.68 (d, 1H, J = 8 Hz); 7.45 (s, 1H); 6.03 (s, 1H); 3.02–2.86 (m, 2H); 2.43–2.20 (m, 2H); 2.05 (s, 6H) |
| CH$_2$—C$_6$H$_5$ | * | 50.60  3.66  11.06<br>50.60  3.81  10.89 | | | 122–124 | 11.07 (bs, 1H); 8.48 (s, 1H), 8.25 (bs, 1H), 7.92 (d,1H, J = 8 Hz); 7.63 (d, 1H, J = 8 Hz); 7.50 (s, 1H); 7.35–7.25 (m, 5H); 6.14 (s, 1H); 4.05 (s, 2H) |
| (CH$_2$)$_2$—C$_6$H$_5$ | * | | | | 177–178 | 11.05 (bs, 1H); 8.45 (s, 1H); 7.95 (d, 1H, J = 8 Hz); 7.75 (bs, 1H); 7.58 (d, 1H, J = 8 Hz); 7.48 (s, 1H); 7.30–7.13 (m, 5H); 6.17 (s, 1H); 3.15–3.00 (m, 2H); 2.76 (t, 1H, J = 7 Hz) |
| (CH$_2$)$_3$—C$_6$H$_5$ | * | | | | 145–147 | 11.06 (bs, 1H); 8.50 (s, 1H); 7.92 (d, 1H, J = 8 Hz); 7.78 (t, 1H, J = 4 Hz); 7.67 (d, 1H, J = 8 Hz); 7.50 (s, 1H); 7.30–7.10 (m, 5H); 6.12 (s, 1H); 2.84 (q, 2H, J = 5 Hz); 2.63–2.50 (m, 2H); 1.71 (quintet, 2H, J = 5 Hz) |
| (CH$_2$)$_4$—C$_6$H$_5$ | ether | 54.09  4.78  9.95<br>53.85  4.80  9.85 | | | 151–153 | 11.05 (bs, 1H); 8.48 (s, 1H); 7.93 (d, 1H, J = 8 Hz); 7.74–7.64 (m, 2H); 7.49 (s, 1H); 6.10 (s, 1H); 2.90–2.80 (m, 2H); 2.53 (t, 2H, J = 5 Hz); 1.62–1.36 (m, 4H) |
| 4-FC$_6$H$_4$ | CHCl$_3$ | 46.95  2.89  10.94<br>46.87  3.02  10.78 | | | 244–245 | 11.09 (bs, 1H); 10.40 (bs, 1H); 8.54 (s, 1H); 7.77 (d, 1H, J = 8 Hz); 7.59 (d, 1H, J = 8 Hz); 7.49 (s, 1H); 7.20–7.05 (m, 4H); 6.13 (s, 1H) |
| CH$_2$—2-furyl | * | | | | 169–170 | 11.02 (bs, 1H); 8.45 (s, 1H); 8.30 (bs, 1H); 7.93 (d, 1H, J = 8 Hz); 7.58–7.54 (m, 1H); 7.48 (s, 1H); 6.39–6.35 (m, 1H); 6.25 (d, 1H, J = 2 Hz); 6.14 (s, 1H); 4.10 (s, 1H) |

*Chromatography on silica gel, elution with 60:40 hexane:ethyl acetate.

EXAMPLE 8

5-(2-Hexylsulfonylphenyl)hydantoin

To a solution of 5-(5-chloro-2-hexylsulfinylphenyl)-hydantoin (4.8 g, 0.014 mol) in glacial acetic acid (50 ml) was added potassium permanganate (2.2 g, 0.014 mol) and water (5 ml). The mixture was stirred at room temperature for 45 minutes then poured into 10% sodium bisulfite solution (50 ml). The resulting solution was extracted with ether, the ethereal extract then dried (MgSO$_4$) and evaporated under reduced pressure. The brown oily residue was chromatographed on silica gel and the product eluted with ethyl acetate:hexane (40:60). Evaporation of the eluate under reduced pressure afforded 1.32 g of product as a white solid (26% yield). M.P. 188°–189° C.

Analysis:

Calc'd. for C$_{15}$H$_{19}$N$_2$O$_4$SCl: 50.21% C; 5.34% H; 7.81% N Found: 50.05% C; 5.23% H; 7.76% N.

The following compounds were prepared in like manner from the corresponding 5-(2-alkylsulfinyl)-hydantoins:

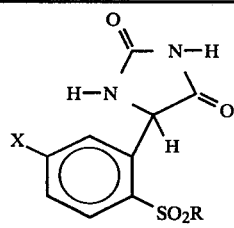

| X | R | Calc'd Found | | | MP (°C.) | 250 MHz NMR |
|---|---|---|---|---|---|---|
| | | % C | % H | % N | | |
| H | $CH_2CH_3$ | | | | 185 (foam) | 11.03 (bs, 1H); 8.54 (s, 1H); 7.98 (d, 1H, J = 8 Hz); 7.83 (t, 1H, J = 8 Hz); 7.66 (t, 1H, J = 8 Hz); 7.55 (d, 1H, J = 8 Hz); 6.25 (s, 1H); 3.50 (q, 2H, J = 8 Hz); 1.15 (t, 3H, J = 8 Hz) |
| H | $(CH_2)_2CH_3$ | | | | 190 (foam) | 11.01 (bs, 1H); 8.55 (s, 1H); 7.98 (d, 1H, J = 8 Hz); 7.81 (t, 1H, J = 8 Hz); 7.65 (t, 1H, J = 8 Hz); 7.56 (d, 1H, J = 8 Hz); 6.23 (s, 1H); 3.55-3.42 (m, 2H); 1.80-1.42 (m, 2H); 0.94 (t, 3H, J = 8 Hz) |
| H | $CH(CH_3)_2$ | | | | 195 (foam) | 11.03 (bs, 1H); 8.55 (s, 1H); 7.98 (d, 1H, J = 8 Hz); 7.81 (t, 1H, J = 8 Hz); 7.66 (t, 1H, J = 8 Hz); 7.56 (d, 1H, J = 8 Hz); 6.18 (s, 1H); 3.71 (septet, 1H); 1.30 (d, 3H, J = 8 Hz); 1.09 (d, 3H, J = 8 Hz) |
| Cl | $(CH_2)_3CH_3$ | 47.20 47.10 | 4.57 4.61 | 8.47 8.42 | 191-192 | 11.09 (bs, 1H); 8.55 (s, 1H); 8.00 (d, 1H, J = 8 Hz); 7.77 (d, 1H, J = 8 Hz); 7.59 (s, 1H); 6.23 (s, 1H); 3.55 (t, 2H, J = 8 Hz); 1.76-1.30 (m, 4H); 0.85 (t, 3H, J = 8 Hz) |
| Cl | $(CH_2)_4CH_3$ | 48.77 48.82 | 4.97 4.99 | 8.12 8.12 | 160-161 | 11.10 (bs, 1H); 8.55 (s, 1H); 8.00 (d, 1H, J = 8 Hz); 7.76 (d, 1H, J = 8 Hz); 7.60 (s, 1H); 6.25 (s, 1H); 3.55 (t, 2H, J = 9 Hz); 1.78-1.18 (m, 6H); 0.84 (t, 3H, J = 8 Hz) |

EXAMPLE 9

Repetition of the procedure of Example 1, but using the appropriate benzoic acid derivative (II) as reactant affords the following compounds:

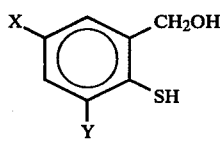

| X | Y | X | Y |
|---|---|---|---|
| Br | H | $CH_3$ | $NO_2$— |
| H | Cl | $CH_3$ | $NH_2$ |
| H | Br | $CH_3$ | Cl |
| H | F | $n-C_3H_7$ | Cl |
| F | H | $CH_3$ | F |
| $CH_3$ | H | $NH_2$ | F |
| $n-C_4H_9$ | H | $NH_2$ | $CF_3$ |
| $NH_2$ | H | F | F |
| $NO_2$ | H | $CH_3$ | $CH_3$ |
| F | $CF_3$ | Cl | $NH_2$ |
| F | $CH_3$ | Br | $NO_2$ |
| $OCH_3$ | H | $OCH_3$ | $OCH_3$ |
| $OCH_3$ | Cl | $CH_3$ | $OCH_3$ |
| Cl | $OCH_3$ | F | $OC_2H_5$ |
| $OC_6H_{13}$ | H | $NH_2$ | $OCH_3$ |

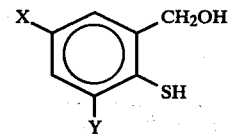

| X | Y | X | Y |
|---|---|---|---|
| $OCH_3$ | $NO_2$ | Br | $OC_2H_5$ |

EXAMPLE 10

The compounds of Examples 1 and 9 are converted by the procedure of Example 2 by reaction with the appropriate alkylating or aralkylating agent RI to compounds having the following formula wherein X and Y are as defined in said Examples and R has the values given below:

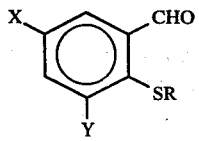

| R | R |
|---|---|
| CH$_3$ | CH$_2$—4-(i-C$_3$H$_7$O)C$_6$H$_4$ |
| n-C$_3$H$_7$ | CH$_2$—2-NH$_2$C$_6$H$_4$ |
| n-C$_6$H$_{13}$ | CH$_2$—3-NH$_2$C$_6$H$_4$ |
| i-C$_4$H$_9$ | CH$_2$—4-NH$_2$C$_6$H$_4$ |
| CH$_2$—O—CH$_3$ | (CH$_2$)$_3$—4-NH$_2$C$_6$H$_4$ |
| CH$_2$—2-ClC$_6$H$_4$ | CH$_2$—4-NO$_2$C$_6$H$_4$ |
| (CH$_2$)$_3$—4-FC$_6$H$_4$ | CH$_2$—2,4-F$_2$C$_6$H$_3$ |
| (CH$_2$)$_2$—4-ClC$_6$H$_4$ | CH$_2$—2,4-Cl$_2$C$_6$H$_3$ |
| CH$_2$—3-FC$_6$H$_4$ | (CH$_2$)$_3$—2,4-F$_2$C$_6$H$_3$ |
| CH$_2$—4-BrC$_6$H$_4$ | CH$_2$—2-NH$_2$—4-F—C$_6$H$_3$ |
| CH$_2$—2-(CH$_3$)C$_6$H$_4$ | CH$_2$—2-F—4-CH$_3$OC$_6$H$_3$ |
| (CH$_2$)$_2$—4-(CH$_3$)C$_6$H$_4$ | (CH$_2$)$_2$—2-CH$_3$O—4-FC$_6$H$_3$ |
| CH$_2$—4-(C$_6$H$_{13}$)C$_6$H$_4$ | (CH$_2$)$_2$—2-C$_4$H$_9$O—4-FC$_6$H$_3$ |
| CH$_2$—4-(CH$_3$O)C$_6$H$_4$ | CH$_2$—2-(C$_2$H$_5$O)C$_6$H$_4$ |
| (CH$_2$)$_3$—3-CH$_3$OC$_6$H$_4$ | (CH$_2$)$_2$—2,4-(CH$_3$)$_2$C$_6$H$_3$ |
| CH$_2$—3-NO$_2$—4-CH$_3$C$_6$H$_3$ | (CH$_2$)$_2$—3,4-F$_2$C$_6$H$_3$ |
| CH$_2$—2,6-F$_2$C$_6$H$_3$ | (CH$_2$)$_2$—2-CH$_3$—6-FC$_6$H$_3$ |
| CH$_2$—3,5-Cl$_2$C$_6$H$_3$ | (CH$_2$)$_3$—C$_6$H$_5$ |
| (CH$_2$)$_3$—2,5-(CH$_3$)$_2$C$_6$H$_5$ | CH$_2$—3-C$_2$H$_5$C$_6$H$_4$ |
| CH$_2$—2-NH$_2$—4-NO$_2$C$_6$H$_3$ | (CH$_2$)$_4$—C$_6$H$_5$ |
| (CH$_2$)$_4$—4-FC$_6$H$_4$ | (CH$_2$)$_4$—2,4-Cl$_2$C$_6$H$_3$ |
| (CH$_2$)$_4$—4-H$_2$NC$_6$H$_4$ | |

EXAMPLE 11

Following the procedure of Example 3, the benzaldehyde derivatives of Example 10 are converted to the corresponding hydantoins of the formula below wherein X, Y and R are as defined in Example 10.

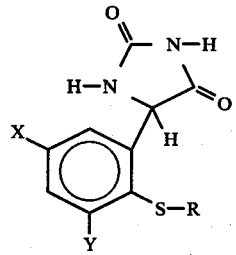

EXAMPLE 12

Oxidation of the hydantoins of Example 11 by the procedure of Example 4 affords the sulfinylphenyl hydantoins having the formula

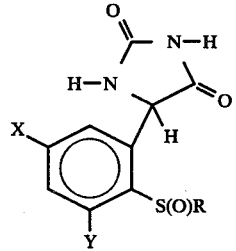

wherein X, Y and R are as defined in Example 11.

EXAMPLE 13

The 5-(2-thiophenyl)hydantoins of Example 11 are oxidized according to the procedure of Example 5 to give the corresponding compounds of the formula below wherein X, Y and R are as defined in Example 11

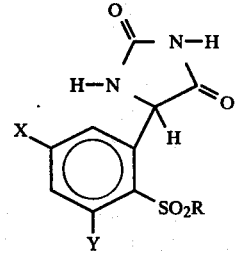

EXAMPLE 14

The compounds of Example 11 wherein R is methoxymethyl are converted by the procedure of Example 6 to the corresponding chlorosulfonyl derivatives of the formula

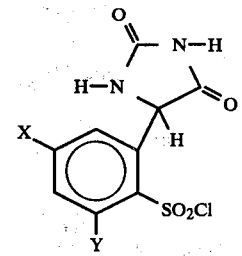

wherein X and Y are as defined in Example 11.

EXAMPLE 15

Utilizing the procedure of Example 7, the (2-chlorosulfonylphenyl)hydantoins of Example 14 are converted to the following sulfonamido derivatives by reaction with the appropriate amine R$^1$NH$_2$

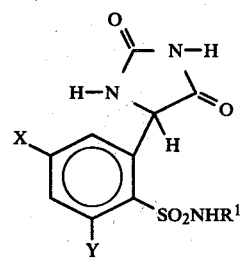

wherein X and Y are as defined in Example 14.

| R$^1$ | R$^1$ |
|---|---|
| H | (CH$_2$)$_2$—4-FC$_6$H$_4$ |
| CH$_3$ | (CH$_2$)$_2$—4-ClC$_6$H$_4$ |
| n-C$_3$H$_7$ | (CH$_2$)$_4$—C$_6$H$_5$ |
| n-C$_6$H$_{13}$ | (CH$_2$)$_4$—2-F—C$_6$H$_4$ |
| sec-C$_4$H$_9$ | (CH$_2$)$_4$—4-Cl—C$_6$H$_4$ |
| CH$_2$CH$_2$OH | furfuryl |
| (CH$_2$)$_6$OH | CH$_2$—4-FC$_6$H$_4$ |
| CH$_2$—4-ClC$_6$H$_4$ | CH$_2$—2-ClC$_6$H$_4$ |
| CH$_2$—2-FC$_6$H$_4$ | CH$_2$—3-ClC$_6$H$_4$ |
| CH$_2$—C$_6$H$_5$ | (CH$_2$)$_2$—C$_6$H$_5$ |

We claim:
1. A compound having the formula

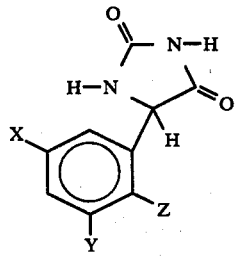

or a pharmaceutically acceptable salt thereof,
wherein each of X and Y is hydrogen, fluoro, chloro, bromo, (C$_{1-6}$)alkyl, (C$_{1-6}$)alkoxy, trifluoromethyl, amino or nitro;
Z is S(O)$_m$R or SO$_2$NHR$^1$;
m is 0, 1 or 2;
R is hydrogen, (C$_{1-6}$)alkyl, chloro, methoxymethyl or

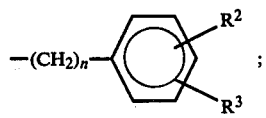

R$^1$ is hydrogen, furfuryl,

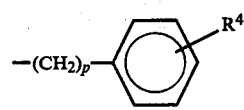

(C$_{1-6}$)alkyl, omega-substituted (C$_{2-6}$)alkyl wherein the substituent is hydroxy or dimethylamino;
wherein R$^4$ is hydrogen, fluoro or chloro;
n is an integer of from 1 to 4; p is 0 or an integer of from 1 to 4;
and each of R$^2$ and R$^3$ is hydrogen, fluoro, chloro, bromo, (C$_{1-6}$)alkyl, (C$_{1-6}$)alkoxy, amino or nitro, with the proviso that when R is chloro, m is 2, and when R$^1$ is hydrogen at least one of X and Y is other than hydrogen.

2. A compound according to claim 1 wherein Z is S(O)$_m$R.

3. A compound according to claim 2 wherein m is 2 and R is (C$_{1-6}$)alkyl.

4. A compound according to claim 3 wherein X is fluoro or chloro and Y is fluoro, chloro, methyl or hydrogen.

5. A compound according to claim 4 wherein X is chloro and Y is hydrogen.

6. The compound according to claim 5 wherein R is methyl.

7. A compound according to claim 4 wherein X is fluoro and Y is hydrogen.

8. The compound according to claim 7 wherein R is methyl.

9. A compound according to claim 2 wherein R is

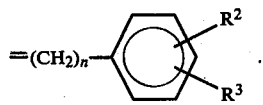

10. A compound according to claim 9 wherein X is fluoro or chloro; Y is hydrogen; m is 2; n is 1; and R$_2$ is hydrogen.

11. The compound according to claim 10 wherein X is chloro and R$_3$ is 4-chloro.

12. A compound according to claim 1 wherein Z is SO$_2$NHR$^1$.

13. A compound according to claim 12 wherein R$^1$ is furfuryl or

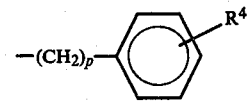

wherein p is 0.

14. A compound according to claim 13 wherein X is fluoro or chloro and Y is hydrogen, fluoro, chloro or methyl.

15. The compound according to claim 14 wherein Y is hydrogen, X is chloro and R$^1$ is

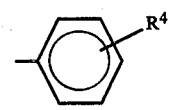

wherein R$^4$ is 4-F.

16. The compound according to claim 14 wherein X is chloro, Y is hydrogen and R$^1$ is furfuryl.

17. A compound according to claim 2 wherein R is methoxymethyl.

18. A compound according to claim 17 wherein X is chloro or fluoro; and Y is hydrogen, fluoro, chloro or methyl.

19. A compound according to claim 2 wherein R is chloro; X is chloro or fluoro and Y is hydrogen, chloro, fluoro or methyl.

20. A method for treating a diabetic host for diabetes associated complications which comprises administering to said host an effective amount of a compound having the formula:

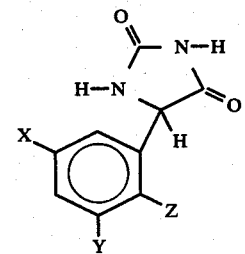

or a pharmaceutically acceptable salt thereof,
wherein each of X and Y is hydrogen, fluoro, chloro, bromo (C$_{1-6}$)alkyl, C$_{1-6}$)alkoxy, trifluoromethyl, amino or nitro;
Z is (SO)$_m$R or SO$_2$NHR$^1$;
m is 0, 1 or 2;
R is hydrogen, (C$_{1-6}$)alkyl, chloro, methoxymethyl or $R^1$ is hydrogen, furfuryl,
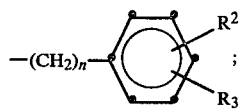
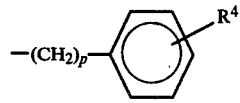
$(C_{1-6})$alkyl, omega-substituted $(C_{2-6})$alkyl wherein the substituent is hydroxy or dimethylamino;
wherein $R^4$ is hydrogen, fluoro or chloro;
n is an integer of from 1 to 4; p is 0 or an integer of from 1 to 4;
and each of $R^2$ and $R^3$ is hydrogen, fluoro, chloro, bromo, $(C_{1-6})$alkyl, $(C_{1-6})$alkoxy, amino or nitro, with the proviso that when R is chloro, m is 2.
* * * * *